US010139656B2

(12) United States Patent
Jing et al.

(10) Patent No.: US 10,139,656 B2
(45) Date of Patent: Nov. 27, 2018

(54) ALIGNMENT FILM DETECTING DEVICE AND ALIGNMENT FILM DETECTING METHOD

(71) Applicants: BOE TECHNOLOGY GROUP CO., LTD., Beijing (CN); HEFEI BOE OPTOELECTRONICS TECHNOLOGY CO., LTD., Anhui (CN)

(72) Inventors: Yangkun Jing, Beijing (CN); Changjun Jiang, Beijing (CN)

(73) Assignees: BOE TECHNOLOGY GROUP CO., LTD., Beijing (CN); HEFEI BOE OPTOELECTRONICS TECHNOLOGY CO., LTD., Anhui (CN)

( * ) Notice: Subject to any disclaimer, the term of this patent is extended or adjusted under 35 U.S.C. 154(b) by 40 days.

(21) Appl. No.: 15/098,384

(22) Filed: Apr. 14, 2016

(65) Prior Publication Data
US 2016/0343123 A1     Nov. 24, 2016

(30) Foreign Application Priority Data

May 19, 2015  (CN) .......................... 2015 1 0257769

(51) Int. Cl.
*G02F 1/13* (2006.01)
*G06T 7/00* (2017.01)
*G01N 23/18* (2018.01)

(52) U.S. Cl.
CPC ............... *G02F 1/13* (2013.01); *G01N 23/18* (2013.01); *G06T 7/0006* (2013.01);
(Continued)

(58) Field of Classification Search
CPC ......... G01N 23/00; G02F 1/13; G06T 7/0006; G06T 2207/10116; G06T 2207/30121
See application file for complete search history.

(56) References Cited

U.S. PATENT DOCUMENTS 4,877,940 A * 10/1989 Bangs .................. B23Q 35/127
                                                 219/124.34
7,653,226 B2 * 1/2010 Guhring .................. G06T 15/08
                                                 382/128
(Continued)

FOREIGN PATENT DOCUMENTS

CN          102023398 A       4/2011
CN          103257465 A  *    8/2013    ............. G09G 3/006

OTHER PUBLICATIONS

Peddada et al., "Separating a Wafer of Light Emitting Devices "U.S. Appl. No. 61/896,836, filed Oct. 29, 2013, 21 pages.*
(Continued)

*Primary Examiner* — Mekonen Bekele
(74) *Attorney, Agent, or Firm* — Brooks Kushman P.C.

(57) ABSTRACT

The present disclosure provides in some embodiments an alignment film detecting device including: an imaging unit configured to obtain image information of the alignment grooves on the alignment film of the substrate; and an image processing unit configured to determine whether there is a defect in the alignment grooves on the alignment film based on the image information. According to the alignment film detecting device and the alignment film detecting method provided the present disclosure, the defect of the alignment film on the substrate may be detected, and the image information of the alignment grooves on the alignment film of the substrate may be obtained by the imaging unit, and a recognizing process may be implemented by the image processing unit based on the image information, so that it may accurately determine whether there is a defect in the alignment grooves. As compared with a method of manually detecting the defect in the alignment grooves by vapor in a conventional alignment film detecting technique, it may overcome disadvantages of manually detecting the defect in the alignment grooves of the substrate, such as low recognition rate, being vulnerable to false detection, and inefficient detection, so as to improve detection efficiency as well as accuracy and credibility of the detection result.

19 Claims, 3 Drawing Sheets

(52) U.S. Cl.
CPC .. *G01N 2223/611* (2013.01); *G01N 2223/646* (2013.01); *G06T 2207/10116* (2013.01); *G06T 2207/30121* (2013.01)

(56) References Cited

U.S. PATENT DOCUMENTS

| | | | | |
|---|---|---|---|---|
| 2002/0072195 | A1* | 6/2002 | Anma | H01L 21/76224 438/401 |
| 2005/0011861 | A1* | 1/2005 | Choo | C23C 16/26 216/62 |
| 2005/0254045 | A1* | 11/2005 | Weiss | G01N 21/95 356/237.5 |
| 2008/0309698 | A1 | 12/2008 | Nakano et al. | |
| 2016/0124254 | A1* | 5/2016 | Yoon | G02F 1/1333 349/110 |
| 2016/0260865 | A1* | 9/2016 | Peddada | B28D 5/0011 |
| 2016/0371832 | A1* | 12/2016 | Jing | H04N 5/33 |
| 2018/0144510 | A1* | 5/2018 | Lachaine | A61B 6/032 |

OTHER PUBLICATIONS

1st Chinese Office Action, English Translation.
CN102023398A, English Abstract and Machine Translation.
CN103257465A, English Abstract and Machine Translation.
First Office Action for Chinese Application No. 201510257769.6, dated May 4, 2017, 5 Pages.

* cited by examiner

ALIGNMENT FILM DETECTING DEVICE AND ALIGNMENT FILM DETECTING METHOD

CROSS REFERENCE OF RELATED APPLICATION

The present application claims the priority of Chinese patent application No. 201510257769.6 filed on May 19, 2015, the disclosure of which is incorporated herein by reference in its entirety.

TECHNICAL FIELD

The present disclosure relates to the field of display technology, in particular to an alignment film detecting device and an alignment film detecting method.

BACKGROUND

Alignment films are arranged on an array substrate and a color filer substrate of a thin film transistor liquid crystal display (TFT-LCD) respectively, and grooves are arranged on each alignment film in a predetermined direction and configured for causing liquid crystal molecules to be arranged in the direction of the grooves in a condition that the liquid crystal molecules are not affected by an electric field. The alignment film having an alignment function is generally formed by a polyimide (PI) film in a process of: rubbing a PI film coated and solidified on a glass substrate by a roller being wrapped up by rubbing cloth, so as to form the grooves on a surface of the PI film in the predetermined direction.

During the process of forming the alignment film, since the rubbing cloth may have defect such as uneven width, foreign substances being adhered to a surface, an affection by impurities during the process of rubbing for forming the grooves or etc., the grooves on the alignment film formed by such processes may have a direction, a shape, a depth and etc. that deviate from a desired direction, a desired shape, a desired depth and etc. respectively, namely a rubbing mura is generated, so that the alignment performance is adversely affected. Thus, it is necessary to detect whether there is a defect in the grooves on the alignment film after the alignment film has been formed.

In related art, it generally determines whether there is a defect in the grooves on the alignment film by a method including following steps.

Water vapor is sprayed to a surface of the alignment film on the glass substrate by a vapor spray nozzle which is typically hold by an operator manually, so as to form water particles on surfaces of the grooves. Meanwhile, a region of the alignment film where the water vapor is sprayed by an intense light is irradiated, so as to determine whether there is a defect in the grooves on the alignment film manually (a diffused reflection may occur at a position of the defect in the grooves when the light ray is transmitted through the position) by viewing the grooves irradiated by the intense light (it typically generates a bright line, i.e. a line mura).

When the defect in the grooves on the alignment film is detected, the position of the defect in the grooves is generally measured by a ruler. A measurement value is manually converted to an approximate position of a defect in the rubbing cloth corresponding to the position of the defect in the grooves, and the defect in the rubbing cloth is repaired. Then the PI film is rubbed again and it detects whether there still exists the defect in the grooves on the alignment film by the above vapor detection method, so as to determine whether the defect in the rubbing cloth is eliminated.

However, the above vapor detection method has following disadvantages.

Firstly, the water vapor is sprayed and adhered to the glass substrate and the surface of the alignment film. Thus, during the process of forming the water droplets, some of the formed water droplets continue to disappear due to facts of air movement, evaporation and so on, so that a period of spraying the vapor for the detection is prolonged, and the efficiency is lowered.

Secondly, the efficiency of the above method for detecting whether there is the defect in the grooves on the alignment film is low because it is implemented manually. In addition, the credibility of the detection result may be low because different operators may have different standards for the detection by their eyes respectively.

Thirdly, when the glass substrate and the alignment film are large, some regions in the glass substrate and the alignment film may be unreachable by the vapor spray nozzle hold by the operator, so that the defect in grooves in these regions of the alignment film is undetectable.

Fourthly, the vapor spray nozzle is typically in direct connection with a water tank being heated. As a result, when a water level in the tank is high, it is possible that some water droplets in the tank are transmitted to the vapor spray nozzle and sprayed to the alignment film, and thus the subsequent process is adversely affected.

Fifthly, the grooves on the alignment film are required to be smaller as a capability for detecting the alignment grooves in the TFT LCD is becoming stronger. Since an evenness of the water droplets formed on the surfaces of the glass substrate and the alignment film is poor and observation limitation on human eyes, the above vapor detection method cannot satisfy the requirement of detecting the defect in the grooves on the alignment film of the TFT LCD which has a strong detection capability for detecting the alignment grooves.

Furthermore, the above vapor detection method is implemented manually, so that the position of the defect in the rubbing cloth generally cannot be accurately determined by the manual computation, and thus it is impossible that the defect in the rubbing cloth is eliminated by one-time positioning and repairing. As a result, the above process has to be repeated several times. If the defect in the rubbing cloth still has not been eliminated by repeating the above process several times, the rubbing cloth has to be replaced by a new one, which is expensive and laborious, and also reduce utilization of the production line.

SUMMARY

An object of the present disclosure is to provide an alignment film detecting device and an alignment film detecting method, so as to improve detection efficiency as well as accuracy and credibility of the detection result.

The technical solutions of the present disclosure are as follows.

In one aspect, the present disclosure provides in some embodiments an alignment film detecting device for detecting alignment grooves formed on an alignment film of a substrate. The alignment film detecting device may include: an imaging unit configured to obtain image information of the alignment grooves on the alignment film of the substrate; and an image processing unit configured to determine whether there is a defect in the alignment grooves on the alignment film based on the image information, and connected to the imaging unit.

Furthermore, the imaging unit may include: a ray source configured to generate rays that are to be transmitted through the substrate including the alignment film; and a receiving module arranged to be opposite to a position of the ray source relative to the substrate, and configured to receive the rays having been transmitted through the substrate and generate a grey scale stripe image. The grey scale stripe image may include first grey scale image regions corresponding to the alignment grooves on the alignment film and second grey scale image regions corresponding to portions between every two neighboring ones of the alignment grooves. And the first grey scale image regions and the second grey scale image regions may be arranged alternately.

Furthermore, the image processing unit may include: a first measuring module configured to convert interface positions of the grey scale values representing gradient variation between the first grey scale image regions and the second grey scale image regions into width values of the alignment grooves on the alignment film based on a first predetermined correspondence; and a first determining module configured to compare the width values of the alignment grooves obtained by the first measuring module with a predetermined reference width threshold value, so as to determine whether the widths of the alignment grooves on the alignment film are qualified.

Furthermore, the widths of the alignment grooves may be each within a range of 0.05 μm-0.2 μm; and the alignment grooves may be each of a straight stripe shape.

Furthermore, the image processing unit may also include: a second measuring module configured to convert the grey scale values of the first grey scale image regions into depth values of the alignment grooves on the alignment films based on a second predetermined correspondence; and a second determining module configured to compare the depth values of the alignment grooves obtained by the second measuring module with a predetermined reference depth threshold value, so as to determine whether the depths of the alignment grooves on the alignment film are qualified.

Furthermore, the ray source may include an X-ray source configured to emit X rays; the receiving module may include an X-ray sensitive lens configured to receive the X rays and generate the grey scale stripe image based on the received X rays.

Furthermore, a light diaphragm may be arranged between the X-ray sensitive lens and the substrate and configured to adjust an intensity of the X-rays transmitted through the substrate, so as to stabilize a radiation amount of the X-rays received by the X-ray sensitive lens.

Furthermore, the X-ray source may consist of an X-ray array source; and the X-ray sensitive lens may consist of an X-ray sensitive charge-coupled-device (CCD) flat panel detector (FPD).

Furthermore, the image processing unit may also include: a third determining module configured to determine that there is a foreign substance in a detecting region when the grey scale values of the detecting region are greater than a predetermined grey scale threshold value.

Furthermore, there may be at least two imaging units. The receiving module of any one of the imaging units may receive the rays transmitted through the substrate and emitted by the ray source of another one of the imaging units, and generate the grey scale stripe image.

Furthermore, the alignment film detecting device may also include a moving mechanism configured to move the imaging units to change an angle of the rays emitted by the ray source.

Furthermore, the moving mechanism may include: an arc rail circularly extending from a side of the substrate to the other side of the substrate. The imaging unit may be movable on the arc rail to change an angle of the rays that are incident on the substrate, and a position of the source ray relative to the substrate and a position of the receiving module relative to the substrate on the arc rail in the imaging unit are exchangeable with each other, so as to combine a front-side grey scale stripe image generated by the rays being incident on a region of a front side of the substrate and a back-side grey scale stripe image generated by the rays being incident on the same region of a back side of the substrate.

Furthermore, the X-ray sensitive CCD flat panel detector may include: a lens driving device, an X-ray conversion screen and a CCD image rectangular plane sensor array. After the X rays emitted by the X-ray source have been transmitted through the substrate, an intensity distribution of the X-rays carries information of the alignment film on the substrate, and the X-rays may be incident on the X-ray conversion screen arranged opposite to the substrate, so as to be converted into a visible light image by the X-ray conversion screen. An intensity of visible light rays emitted from each point may be proportional to radiation amount of the X-rays that are incident on the X-ray conversion screen. The X-ray conversion screen may be in direct contact with a photosensitive surface of the CCD image rectangular plane sensor array. And the visible light rays emitted from the X-ray conversion screen may be directly received by the photosensitive surface of the CCD image rectangular plane sensor array, so as to generate the grey scale stripe image. And the grey scale stripe image may be processed by an analog to digital (A/D) converter, and transmitted to the image processing unit to gather, store and process the image information, and then it is determined whether there is a defect in the alignment grooves based on the obtained image information or other analyses are carried out.

Furthermore, the imaging unit may further include: a high transparent prism and a cylindrical lens. The X rays may be emitted by the X-ray source under the control of an X-ray controller, adjusted by the cylindrical lens to be in a horizontal direction, reflected by the high transparent prism and incident on the substrate, transmitted through the substrate, and then incident on the X-ray conversion screen.

Furthermore, the alignment film detecting device may also include: an image management unit configured to manage the generated grey scale stripe image in classification, and establish an image database for the alignment grooves on the alignment film.

In another aspect, the present disclosure provides in some embodiments a method for detecting alignment grooves formed on an alignment film of a substrate, the method including steps of: obtaining image information of the alignment grooves on the alignment film of the substrate; and determining whether there is a defect in the alignment grooves on the alignment film based on the image information.

Furthermore, in the method, the step of obtaining image information of the alignment grooves on the alignment film of the substrate may include steps of: generating rays that are to be transmitted through the substrate including the alignment film, receiving the rays having been transmitted through the substrate, and generating a grey scale stripe image. The grey scale stripe image may include first grey scale image regions corresponding to the alignment grooves and second grey scale image regions corresponding to portions between every two neighboring ones of the alignment grooves. And the first grey scale image regions and the second grey scale image regions may be arranged alternately.

The step of determining whether there is a defect in the alignment grooves on the alignment film based on the image information may include steps of: converting interface positions of the grey scale values representing gradient variation between the first grey scale image regions and the second grey scale image regions into width values of the alignment grooves on the alignment film based on a first predetermined correspondence; and comparing the obtained width values of the alignment grooves with a predetermined reference width threshold value, so as to determine whether the widths of the alignment grooves on the alignment film are qualified.

Furthermore, in the method, the step of determining whether there is a defect in the alignment grooves on the alignment film based on the image information may include steps of: converting the grey scale values of the first grey scale image regions into depth values of the alignment grooves based on a second predetermined correspondence; and comparing the obtained depth values of the alignment grooves with a predetermined reference depth threshold value, so as to determine whether the depths of the alignment grooves on the alignment film are qualified.

Furthermore, in the method, the step of generating a grey scale stripe image may include steps of: transmitting the rays onto a front side of the substrate to generate a front side grey scale stripe image, transmitting the rays onto a back side of the substrate to generate a back side grey scale stripe image, and combining the front side grey scale stripe image and the back side grey scale stripe image on the same region to obtain the grey scale stripe image for measuring the alignment grooves on the alignment film.

Furthermore, the method may also include: changing an angle of the rays emitted by the ray source and detecting a corresponding region of the substrate when the grey scale value of the region in the grey scale stripe image is greater than a predetermined grey scale threshold value.

The beneficial effects of the present disclosure are as follows.

According to the alignment film detecting device and the alignment film detecting method provided by embodiments of the present disclosure, the defect of the alignment film on the substrate may be detected, and the image information of the alignment grooves on the alignment film of the substrate may be obtained by the imaging unit, and a recognizing process may be implemented by the image processing unit based on the image information, so that it may accurately determine whether there is a defect in the alignment grooves. As compared with a method of manually detecting the defect in the alignment grooves by vapor in a conventional alignment film detecting technique, it can overcome disadvantages of manually detecting the defect in the alignment grooves of the substrate, such as low recognition rate, being vulnerable to false detection, and inefficient detection, so as to improve detection efficiency as well as accuracy and credibility of the detection result.

According to the alignment film detecting device in a further technical solution of the present disclosure, a ray source may generate X-rays that are to be transmitted through the substrate, and a grey scale stripe image is generated and recognized, so that a width and a depth of each alignment groove in the alignment film may be accurately measured. The static electricity generated by the rubbing process may be eliminated by the X-ray scanning process, so that an independent process for eliminating the static electricity is not required, and thus the production efficiency is improved. Furthermore, a small crack within the substrate caused by the rubbing process may be additionally detected by the X-ray scanning process. In addition, the X-ray detection is relatively simple, robust and fast. Furthermore, the evenness of the structure within the alignment film may be detected by the X-ray detection in which the X-ray is transmitted through the whole alignment film, where the evenness of the alignment film may be determined based on the evenness of the grey scale values of the grey scale stripe image. In addition, the alignment film detecting device may be integrated in the rubbing device, so as to detect and monitor the defect in real time. Thus, a state of the alignment film may be reported quickly, and the rubbing device may be adjusted at a fast speed. As a result, the product quality is effectively controlled, and the defect can be found out very timely, so that yield of the products can be improved.

BRIEF DESCRIPTION OF THE DRAWINGS

In order to illustrate the technical solutions of the present disclosure or the related art in a clearer manner, the drawings desired for the embodiments will be described briefly hereinafter. Obviously, the following drawings merely relate to some embodiments of the present disclosure, and based on these drawings, a person skilled in the art may obtain the other drawings without any creative effort.

DETAILED DESCRIPTION

The present disclosure will be described hereinafter in conjunction with the drawings and embodiments. The following embodiments are for illustrative purposes only, but shall not be used to limit the scope of the present disclosure.

In order to make the objects, the technical solutions and the advantages of the present disclosure more apparent, some technical solutions of the present disclosure will be described hereinafter in a clear and complete manner in conjunction with the drawings and embodiments. Obviously, the following embodiments are merely a part of, rather than all of, the embodiments of the present disclosure, and based on these embodiments, a person skilled in the art may obtain the other embodiments, which also fall within the scope of the present disclosure.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "a" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

The present disclosure will be described hereinafter in conjunction with the drawings and embodiments. The following embodiments are for illustrative purposes only, but shall not be used to limit the scope of the present disclosure.

As compared with the conventional alignment film detecting technique for detecting the defect of the alignment film on the substrate having disadvantages such as low detection efficiency and low accuracy, the present disclosure provides in some embodiments an alignment film detecting device for detecting the defect in the alignment grooves on the alignment film formed on the substrate, so as to improve detection efficiency as well as accuracy and credibility of the detection result.

Figure 1:
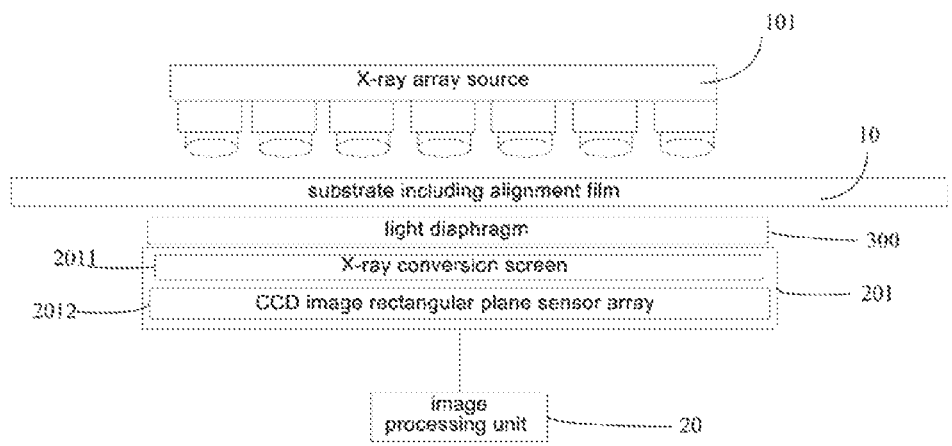
FIG. 1 is a schematic view showing an alignment film detecting device according to an embodiment of the present disclosure.
Figure 2:
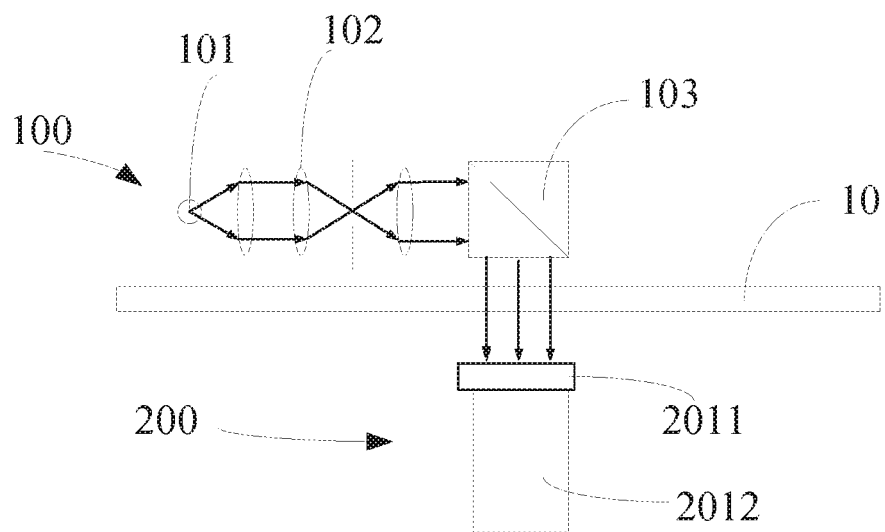
FIG. 2 is a schematic view showing a imaging unit of the alignment film detecting device according to an embodiment of the present disclosure.
Figure 3:
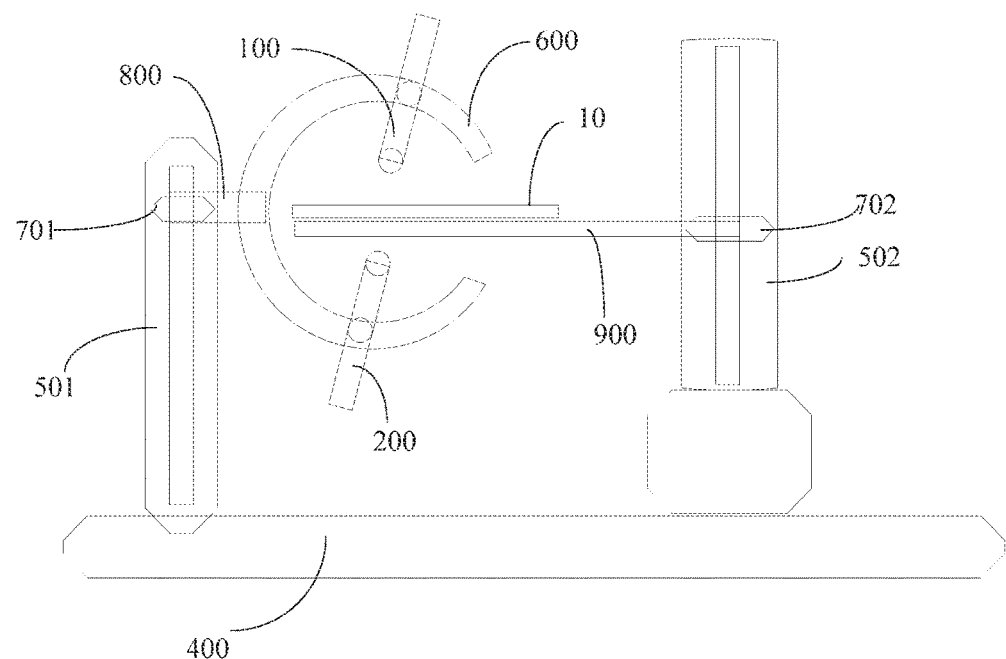
FIG. 3 is a schematic view showing a moving mechanism of the alignment film detecting device according to an embodiment of the present disclosure.

In an embodiment, as illustrated in FIGS. 1-3, the alignment film detecting device includes:

an imaging unit (not shown) configured to obtain image information of the alignment grooves on the alignment film of the substrate 10; and an image processing unit 20 configured to determine whether there is a defect in the alignment grooves on the alignment film based on the image information, and connected to the imaging unit.

According to the alignment film detecting device and the alignment film detecting method of this embodiment, the image information of the alignment grooves on the alignment film of the substrate may be obtained by the imaging unit, and the image information may be recognized by the image processing unit 20, so that it may accurately determine whether there is the defect in the alignment grooves on the alignment film based on the image information. As compared with a method of manually detecting the defect in the alignment grooves by vapor in a conventional alignment film detecting technique, it may overcome disadvantages of manually detecting the defect in the alignment grooves of the substrate, such as low recognition rate, being vulnerable to false detection, and inefficient detection, so as to improve detection efficiency as well as accuracy and credibility of the detection result.

Alternatively, in an embodiment, as illustrated in FIGS. 1, 2, 4 and 5, the imaging unit includes:

a ray source 100 configured to generate rays that are to be transmitted through the substrate 10 including the alignment film; and a receiving module 200 arranged to be opposite to a position of the ray source 100 relative to the substrate 10, and configured to receive the rays having been transmitted through the substrate 10 and generate a grey scale stripe image. Here, the grey scale stripe image includes first grey scale image regions indicated by a sign "a" corresponding to the alignment grooves on the alignment film and second grey scale image regions indicated by a sign "b" corresponding to portions between every two neighboring ones of the alignment grooves, and the first grey scale image regions indicated by the sign "a" and the second grey scale image regions indicated by the sign "b" are arranged alternately.

The image processing unit 20 includes:

a first measuring module configured to convert interface positions of the grey scale values representing gradient variation between the first grey scale image regions indicated by the sign "a" and the second grey scale image regions indicated by the sign "b" into width values of the alignment grooves on the alignment film based on a first predetermined correspondence; and a first determining module configured to compare the width values of the alignment grooves obtained by the first measuring module with a predetermined reference width threshold value, so as to determine whether the widths of the alignment grooves on the alignment film are qualified.

Figure 4:
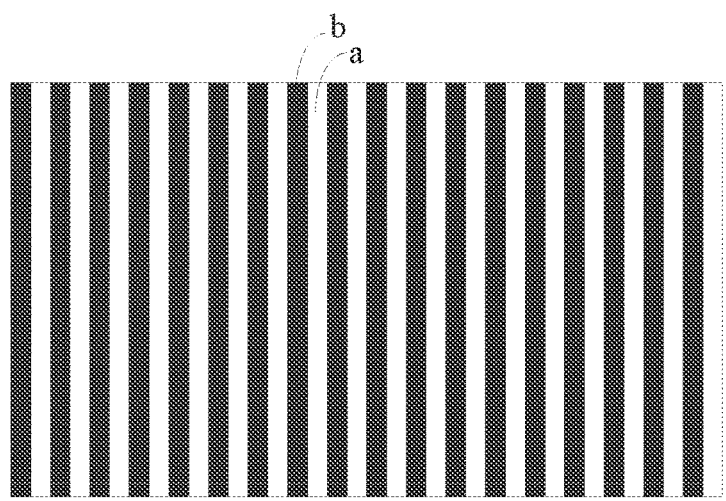
FIG. 4 is a schematic view showing a grey scale stripe image formed by the alignment film detecting device upon detecting the alignment film according to an embodiment of the present disclosure.
Figure 5:
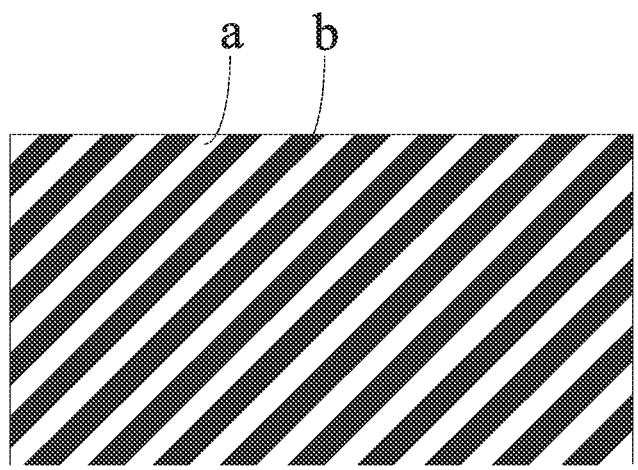
FIG. 5 is a schematic view showing another grey scale stripe image formed by the alignment film detecting device upon detecting the alignment film according to an embodiment of the present disclosure.

In the above solution, the ray source 100 is arranged at one side of the substrate 10 and generates rays that are to be transmitted through the substrate 10, and the receiving module 200 is arranged at the other side of the substrate 10 and receives the rays having been transmitted through the substrate 10. Since a radiation amount of the rays having been transmitted through the alignment grooves on the alignment film is different from a radiation amount of the rays having been transmitted through portions between every two neighboring ones of the alignment grooves, the receiving module 200 may receive the rays and generate the grey scale stripe image presenting intensity variation caused by different grey scale values based on the received rays (as illustrated in FIGS. 4 and 5). The grey scale stripe image includes first grey scale image regions indicated by the sign "a" corresponding to the alignment grooves on the alignment film and second grey scale image regions indicated by the sign "b" corresponding to portions between every two neighboring ones of the alignment grooves. In addition, since the radiation amount of the rays having been transmitted through the regions corresponding to the alignment grooves is greater than the radiation amount of the rays having been transmitted through the portions between every two neighboring ones of the alignment grooves, the grey scale values of the first grey scale image regions indicated by the sign "a" are less than the grey scale values of the second grey scale image regions indicated by the sign "b". In other words, there are bright and dark interface positions of the grey scale values representing gradient variation between the first grey scale image regions indicated by the sign "a" and the second grey scale image regions indicated by the sign "b". The image processing unit 20 may convert the interface positions of the grey scale values representing gradient variation between the first grey scale image regions indicated by the sign "a" and the second grey scale image regions indicated by the sign "b" into width values of the alignment grooves on the alignment film based on a predetermined correspondence, so as to compare the converted width values of the alignment grooves with a predetermined width threshold value of the alignment grooves, and thus determine whether the widths of the alignment grooves on the alignment film are qualified.

It is appreciated that, as illustrated in FIGS. 4 and 5, the grey scale values representing gradient variation indicate positions where the bright and dark variation exists in the grey scale stripe image, which corresponds to the grey scale values representing gradient variation between the first grey scale image regions indicated by the sign "a" and the second grey scale image regions indicated by the sign "b". It is further appreciated that, as illustrated in FIGS. 4 and 5, the alignment grooves on the alignment film are in different directions, and thus the directions of the stripes representing the bright and dark variation in the generated grey scale stripe image are different accordingly. The image processing unit may convert the positions of the grey scale values of the stripes representing gradient variation (i.e. the interface positions of the grey scale values representing gradient variation between the first grey scale image regions indicated by the sign "a" and the second grey scale image regions indicated by the sign "b") into width values of the alignment grooves on the alignment film based on a predetermined correspondence and the directions of the stripes.

It is appreciated that, in the above solutions, the detection of the defect in the alignment film by the rays is implemented by clearly recognizing the grey scale stripe image including bright and dark interfaces. In the embodiments of the present disclosure, a structure of the alignment grooves on the alignment film of the substrate 10 being detected by the alignment film detecting device may be different from a structure of the alignment grooves on the alignment film of the conventional substrate 10. Alternatively, the widths of the alignment grooves are each within a range of 0.05 µm-0.2 µm, so that the alignment grooves on the alignment film of the substrate 10 being detected by the alignment film detecting device may cause a high contrast at the interface of the neighboring regions in the image to facilitate the recognition. As a result, an adverse effect on geometric unsharpness by the width of the material is reduced. Alternatively, the alignment grooves are each of a straight stripe shape, so as to reduce an adverse effect on the geometric unsharpness by edge effect, i.e. reduce an adverse effect on unsharpness of interface positions between the first grey scale image regions indicated by the sign "a" and the second grey scale image regions indicated by the sign "b". As a result, the detection for the defect in the alignment film is facilitated. It is appreciated that the above alignment film detecting device may alternatively be configured to detect the defect in the alignment grooves on the alignment film of the conventional substrate 10.

Furthermore, in an embodiment of the present disclosure, the image processing unit further includes:

a second measuring module configured to convert the grey scale values of the first grey scale image regions indicated by the sign "a" into depth values of the alignment grooves on the alignment films based on a predetermined correspondence; and a second determining module configured to compare the depth values of the alignment grooves obtained by the second measuring module with a predetermined reference depth threshold value, so as to determine whether the depths of the alignment grooves on the alignment film are qualified.

In the above solution, the radiation amounts of the rays having been transmitted through the regions corresponding to the alignment grooves having different depths are different, and thus the grey scale values of the first grey scale image regions indicated by the sign "a" corresponding to the alignment groove having a large depth is less than the grey scale values of the first grey scale image regions indicated by the sign "a" corresponding to the alignment groove having a small depth. As a result, the image processing unit 20 may convert the grey scale values of the first grey scale image regions indicated by the sign "a" into depth values of the alignment grooves on the alignment film based on a predetermined correspondence, so as to compare the converted depths values of the alignment grooves with a predetermined depth threshold value of the alignment grooves, and thus determine whether the depths of the alignment grooves on the alignment film are qualified.

Alternatively, in this embodiment, the image processing unit 20 further includes: a third determining module configured to determine that there is a foreign substance in a detecting region when the grey scale values of the detecting region are greater than a predetermined grey scale threshold value. When the grey scale values of a region in the grey scale stripe image are greater than the predetermined grey scale threshold value, an angle for transmitting the rays is changed, so as to detect the corresponding region in the substrate 10 again, and thus prevent the foreign substance from adversely affecting the detection accuracy.

Furthermore, in the embodiment of the present disclosure, the image processing unit 20 may convert the grey scale values of pixels in the grey scale stripe image into the depth values of the alignment grooves based on the predetermined correspondence, and convert interface positions of the grey scale values representing gradient variation between the first grey scale image regions indicated by the sign "a" and the second grey scale image regions indicated by the sign "b" in the grey scale stripe image into width values of the alignment grooves and based on the direction of the grey scale stripe image. The above correspondence may be determined in advance by a plurality of trails. It is appreciated that, in some other embodiments of the present disclosure, the image processing unit may recognize the image information by other means, so as to determine whether the depths of the alignment grooves are qualified. A detailed explanation of examples of such other means is omitted herein.

Furthermore, in the embodiments of the present disclosure, as illustrated in FIGS. 1 and 2, the ray source 100 includes an X-ray source 101 configured to emit X rays; and the receiving module 200 includes an X-ray sensitive lens 201 configured to receive the X rays and generate the grey scale stripe image based on the received X rays.

In the above solution, the X-rays are transmitted through the substrate 10 to form the grey scale stripe image. Air near a surface of the substrate 10 may be decomposed into ionized gas by high energy of the X-rays, and the ionized gas may neutralize the static electricity which is produced by the rubbing process and accumulated on the surface of the substrate 10, so that poor alignment and detection error may be greatly improved. The ray source 100 produces positive ions and negative ions in equal amount while operating to generate the X-rays, so as to eliminate the static electricity efficiently. The static electricity in an irradiation region of the X-rays may be eliminated. In a conventional alignment film detecting technique, a static electricity eliminating device is typically required to eliminate the static electricity which is produced by the rubbing process and accumulated on the alignment film of the substrate 10. In contrast, in the embodiment of the present disclosure, the static electric produced by the rubbing process may be eliminated by the X-rays while scanning the X-rays for detecting the defect in the alignment film, so as to save the independent process for eliminating the static electricity and improve the production efficiency. Meanwhile, a small crack within the substrate 10 caused by the rubbing process may be additionally detected by the X-ray scanning process. In addition, the X-ray detection is relatively simple, robust and fast. Furthermore, the process of eliminating the static electricity by the X-rays has the following advantages: (1) the irons are transmitted by light wave instead of air flow; (2) soft X-rays produces the irons in high density which are capable of eliminating the static electricity quickly and efficiently; (3) the positive ions and the negative ions may be produced in equal amount simultaneously, so that the positive ions and the negative ions are equalized and occurrence of overcharging is avoided; (4) the environment and the object to be eliminated are prone to being contaminated during a process of transmitting the ions by the airflow, and the ray source 100 may save a process of cleaning dust on electrodes which is absorbed when the electrodes discharge for ionization; (5) a photoionization static electricity eliminator may irradiate soft X-rays (3-9.5 kev) for ionization without producing any ozone; (6) the photoionization static electricity eliminator eliminates the static electricity by the soft X-rays instead of corona discharges of the electrodes which may produce electromagnetic noise; and (7) the static electricity on a fast-moving object or a powder product may be eliminated instantaneously.

Furthermore, in the embodiments of the present disclosure, the X-ray source 101 consists of an X-ray array source; and the X-ray sensitive lens 201 consists of an X-ray sensitive CCD FPD.

As illustrated in FIGS. 1-3, in the alignment film detecting device of this embodiment, the X-ray sensitive CCD FPD may include: a lens driving device (not shown), an X-ray conversion screen 2011 and a CCD image rectangular plane sensor array 2012. After the X rays emitted by the X-ray source 101 have been transmitted through the substrate 10, an intensity distribution of the X-rays carries information of the alignment film on the substrate 10, and the X-rays are incident on the X-ray conversion screen 2011 arranged opposite to the substrate, so as to be converted into a visible light image by the X-ray conversion screen 2011. An intensity of visible light rays emitted from each point is proportional to radiation amount of the X-rays that are incident on the X-ray conversion screen, the X-ray conversion screen 2011 is in direct contact with a photosensitive surface of the CCD image rectangular plane sensor array 2012, and the visible light rays emitted from the X-ray conversion screen 2011 is directly received by the photosensitive surface of the CCD image rectangular plane sensor array 2012, so as to generate the grey scale stripe image. The grey scale stripe image is processed by an analog to digital (A/D) converter, and transmitted to the image processing unit 20 (not shown in FIG. 2) to gather, store and process the image information, and then it is determined whether there is a defect in the alignment grooves based on the obtained image information or other analyses are carried out.

Alternatively, as illustrated in FIG. 2, the imaging unit may further include: a high transparent prism 103 and a cylindrical lens 102, where the X rays are emitted by the X-ray source 101 under the control of an X-ray controller, adjusted by the cylindrical lens 102 to be in a horizontal direction, reflected by the high transparent prism 103 and incident on the substrate 10, transmitted through the substrate, and then incident on the X-ray conversion screen 2011. In the above solution, the X-rays to be incident on the substrate are caused to be in parallel, so as to facilitate the process of imaging.

In addition, a control kernel of the whole imaging unit is a programmable logic controller (PLC) which is responsible for coordinating the operation of each part. The PLC is further configured to cooperate with the interface chip of the video signal transmitting line, so as to implement a communication between the imaging processing unit 20 and the imaging unit. The above communication is implemented to deliver the command transmitted by the image processing unit 20 and return the image information to the image processing unit 20. For example, the PLC may include two complex programmable logic devices (CPLDs) which are in low power consumption and generate time sequences required by the system. A first one of the CPLDs is generally configured to generate addresses and read/write control signals for controlling a frame memory, and a second one of the CPLDs is generally configured to generate driving time sequences required by the X-ray sensitive CCD FPD. Some signals are communicated between these two CPLDs. Waveforms of the driving time sequences generated by the second CPLD are transmitted through the driver, and then loaded to the X-ray sensitive CCD FPD. The driving is implemented to generate pulsed voltage required by the X-ray sensitive CCD FPD while generating a driving current. The driver should have sufficient driving capacity to improve efficiency of transferring charges and ensure the image quality, because the X-ray sensitive CCD FPD has large gate capacitors and high driving operation frequency.

A signal of the X-ray sensitive CCD FPD is transmitted to an analogy front end which is generally responsible for processing an analogy signal outputted by the X-ray sensitive CCD FPD. The outputted analogy signal is followed by the front end, and transmitted through level transfer and low noise amplification circuit, so as to output a signal which meets a requirement of quantitative level by the A/D converter. Finally, the signal is inputted into and converted by the A/D converter. The converted digital image signal is temporarily stored in the frame memory under the control of the CPLD. When the image processing unit 20 tends to obtain the image, the PLC and the interface chip of the video signal transmitting line are responsible to transmit the image data in the frame memory to the image processing unit 20 via a universal serial bus (USB).

A core part of the whole imaging unit is the X-ray sensitive CCD FPD, which plays a key role for determining the imaging quality of the system. The X-ray sensitive CCD FPD obtains the image indirectly, and generally consists of a phosphor or scintillator layer, an amorphous silicon (a-Si) layer functioning as photodiodes, and a thin film transistor (TFT) array. After being exposed by the X-rays, the above phosphor or scintillator layer may convert photons of the X-rays to visible light rays, which are converted to image signals by the a-Si layer functioning as the photodiodes and transmitted through the TFT array, so as to obtain digital grey scale stripe image.

For example, the image processing unit 20 may be implemented by a computer running an image processing software. The digital grey scale stripe image gathered by the X-ray sensitive CCD FPD is transmitted to the computer, which obtains the widths and depths of the alignment grooves by measuring the grey scale stripe image. For example, the image processing unit 20 may further include a signal processing module for the A/D conversion.

The image processing software has a modularization structure, and includes a USB interface driving module, an image obtaining module, an image processing module and an image management module. For example, the image processing software is written in C++ programming language and runs on a Windows platform.

In particular, a main function of each module is as follows:

(1) The USB interface driving module is configured for a data communication between the computer and the imaging unit.

(2) The image obtaining module is configured for controlling an exposure of the X-ray sensitive CCD FPD, reading an image data stream, combining the image data stream into the grey scale stripe image, and temporarily storing the image into the computer.

(3) The image processing module is configured for measuring the depths and widths in the alignment grooves on the alignment film based on the grey scale stripe image, and includes:

a first measuring module configured to convert interface positions of the grey scale values representing gradient variation between the first grey scale image regions indicated by the sign "a" and the second grey scale image regions indicated by the sign "b" into width values of the alignment grooves on the alignment film based on a predetermined correspondence;

a first determining module configured to compare the width values of the alignment grooves obtained by the first measuring module with a predetermined reference width threshold value, so as to determine whether the widths of the alignment grooves on the alignment film are qualified;

a second measuring module configured to convert the grey scale values of the first grey scale image regions indicated by the sign "a" into depth values of the alignment grooves on the alignment films based on a predetermined correspondence;

a second determining module configured to compare the depth values of the alignment grooves obtained by the second measuring module with a predetermined reference depth threshold value, so as to determine whether the depths of the alignment grooves on the alignment film are qualified; and a third determining module configured to determine that there is a foreign substance in a detecting region when the grey scale values of the detecting region are greater than a predetermined grey scale threshold value.

(4) The image management module is configured to manage the generated grey scale stripe image in classification, and establish an image database for the alignment grooves on the alignment film, so as to facilitate the images in time sequence to be retrieved, browsed and compared, and convert a report to an electronic document for reference.

Furthermore, in the embodiment of the present disclosure, it is necessary to calibrate the alignment film detecting device, so as to secure a precision of the obtained image information.

Furthermore, in the embodiments of the present disclosure, a light diaphragm 300 is arranged between the X-ray sensitive lens 201 and the substrate 10. The light diaphragm 300 is configured to adjust an intensity of the X-rays transmitted through the substrate 10, so as to stabilize a radiation amount of the X-rays received by the X-ray sensitive lens 201.

Furthermore, in the embodiment of the present disclosure, there are at least two imaging units, where the receiving module 200 of any one of the imaging units receives the rays transmitted through the substrate 10 and emitted by the ray source 100 of another one of the imaging units, and generates the grey scale stripe image. In the above solution, there are at least two imaging units, the ray source 100 and the receiving module 200 of one imaging unit is arranged opposite to the ray source 100 and the receiving module 200 of another imaging unit relative to a position of the substrate 10. The X-ray sensitive lens of any one of the imaging units receives the X-rays transmitted through the substrate 10 and emitted by the ray source 100 of another one of the imaging units, and generates the grey scale stripe image. As a result, the grey scale stripe images corresponding to a same region of the substrate 10 may be formed by at least two imaging units respectively, and then the grey scale stripe images are combined, so as to prevent an occurrence of error which is for example caused by the foreign substance, and improve the precision of the detection.

Furthermore, in the embodiment of the present disclosure, the alignment film detecting device further includes a moving mechanism configured to move the imaging units to change an angle of the rays emitted by the ray source 100. In the above solution, the moving mechanism may move the imaging units to change an angle of the rays emitted to and being incident on the substrate 10 by the ray source 100, so that the same region may be detected by rays having different incident angles, and thus the precision of the detection may be further improved.

Alternatively, as illustrated in FIG. 3, in the alignment film detecting device, the moving mechanism includes an arc rail 600 circularly extending from a side of the substrate 10 to the other side of the substrate 10. The imaging unit is movable on the arc rail 600 to change an angle of the rays that are incident on the substrate 10, and a position of the source ray 100 relative to the substrate 10 and a position of the receiving module 200 relative to the substrate 10 on the arc rail 600 in the imaging unit are exchangeable with each other, so as to combine a front-side grey scale stripe image generated by the rays being incident on a region of a front side of the substrate 10 and a back-side grey scale stripe image generated by the rays being incident on the same region of a back side of the substrate 10.

In the above solution, the imaging unit is movably arranged on the arc rail 600, and the arc rail 600 is capable of circularly extending from a side of the substrate 10 to the other side of the substrate 10. Thus, the ray source 100 and the receiving module 200 of the same imaging unit are movable along the arc rail 600, so as to change an angle of the rays that are incident on the substrate 10; and the angle of the rays emitted by the ray source 100 and the incident angle of the rays of the receiving module 200 of the same imaging unit may be kept consistent, so as to facilitate the process of imaging. Furthermore, a position of the source ray 100 relative to the substrate 10 and a position of the receiving module 200 relative to the substrate 10 on the arc rail 600 in the same imaging unit are exchangeable with each other, so as to combine a front-side grey scale stripe image generated by the rays being incident on a region of a front side of the substrate 10 and a back-side grey scale stripe image generated by the rays being incident on the same region of a back side of the substrate 10.

It is appreciated that, in the embodiment of the present disclosure, the imaging unit is moved by the moving mechanism along the arc rail 600. However, in another embodiment of the present disclosure, the moving mechanism may move in another manner.

It is appreciated that the exchange of positions of the ray source 100 and the receiving module 200 of the same imaging unit may be implemented as follows.

FIG. 3 is a schematic view showing a moving mechanism of the alignment film detecting device according to an embodiment of the present disclosure. As illustrated in FIG. 3, the moving mechanism of the alignment film detecting device may further include:

a base 400;

a first holder 501 and a second holder 502 arranged on the base 400;

a clamp arm (not shown) configured for clamping the arc rail 600;

a rotating mechanism 800 configured for rotating the clamp arm;

a first moving component 701 configured for moving the clamp arm on the first holder 501, where the first moving mechanism 701 includes a first ball screw and so on;

a mechanical arm 900 for moving the substrate 10;

a second moving component 702 configured for moving the mechanism arm 900 on the second holder 502, where the second moving mechanism 702 includes a second ball screw and so on; and a driving motor (not shown) configured for driving the rotating mechanism 800, the first ball screw and the second ball screw, where the driving motor may be a stepping motor.

The imaging unit is mounted and movable on the arc rail 600, and the ray source 100 and the receiving module 200 of the same imaging unit may be arranged to be in a line, so as to facilitate the process of imaging.

The arc rail 600 is clamped by the clamp arm, the arc rail 600 is rotated with the rotating mechanism 800 by the clamp arm, so that the position of the source ray 100 relative to the substrate 10 and a position of the receiving module 200 relative to the substrate 10 in the same imaging unit may be exchanged with each other, and a front-side grey scale stripe image generated by the rays being incident on a region of a front side of the substrate 10 and a back-side grey scale stripe image generated by the rays being incident on the same region of a back side of the substrate 10 may be combined.

The clamp arm may be movable on the first holder 501 by the first ball screw, and the mechanical arm 900 may be movable on the second holder 502 by the second ball screw, so as to adjust a position of the imaging unit relative to the substrate 10.

In this embodiment, the alignment film detecting device may exchange the position of the source ray 100 relative to the substrate 10 and the position of the receiving module 200 relative to the substrate 10 with each other, and combine the front-side grey scale stripe image generated by the rays being incident on the region of the front side of the substrate 10 and the back-side grey scale stripe image generated by the rays being incident on the same region of the back side of the substrate 10, so as to obtain the grey scale stripe image for measuring the alignment grooves on the alignment film, and avoid an occurrence of an artifact caused by the error of the signal. This is because, when there is an artifact in one of the front-side grey scale stripe image and the back-side grey scale stripe image, there must be no artifact in the other one of the front-side grey scale stripe image and the back-side grey scale stripe image. Thus, it may determine whether there is an error when the front-side grey scale stripe image and the back-side grey scale stripe image are combined, so that the artifact is prevented. Furthermore, in this embodiment, the alignment film detecting device may avoid the interference of the foreign substance by the detection of the imaging unit in different angles.

Furthermore, in this embodiment, when the alignment film detecting device moves the imaging unit by the moving mechanism to detect in a predetermined region of the substrate 10, a plurality of grey scale strip images of the same region may be repeatedly formed in different angles, so as to re-establish data of a three-dimensional image. Alternatively, the alignment film detecting device may further include:

a position sensing device configured for sensing positions corresponding to the positions of the ray source 100 and the receiving module 200, and transmitting a corresponding position signal;

a recording device configured for receiving and recording the position signal corresponding to the positions of the ray source 100 and the receiving module 200 sensed by the position sensing device; and an image re-establishing device configured for re-establishing the image based on the image information read from the receiving module 200 and the position information recorded in the recording device.

In the above solution, the positions of the ray source 100 and the receiving module 200 are applied for the process of capturing, combining and re-establishing by the ray, so as to reduce blurring effect caused by movement, and obtain a more precise grey scale stripe image.

In another aspect, the present disclosure provides in some embodiments a method for detecting alignment grooves formed on an alignment film of a substrate 10, the method includes:

step S1: obtaining image information of the alignment grooves on the alignment film of the substrate 10; and step S2: determining whether there is a defect in the alignment grooves on the alignment film by comparing the image information with a predetermined reference image information.

Alternatively, in the above method, the step S1 may further include steps of: generating rays that are to be transmitted through the substrate 10 including the alignment film, receiving the rays having been transmitted through the substrate 10, and generating a grey scale stripe image. The grey scale stripe image includes first grey scale image regions indicated by a sign "a" corresponding to the alignment grooves and second grey scale image regions indicated by a sign "b" corresponding to portions between every two neighboring ones of the alignment grooves, and the first grey scale image regions indicated by the sign "a" and the second grey scale image regions indicated by the sign "b" are arranged alternately.

The step S2 specifically includes:

step S21: converting interface positions of the grey scale values representing gradient variation between the first grey scale image regions indicated by the sign "a" and the second grey scale image regions indicated by the sign "b" into width values of the alignment grooves on the alignment film based on a first predetermined correspondence; and step S22: comparing the obtained width values of the alignment grooves with a predetermined reference width threshold value, so as to determine whether the widths of the alignment grooves on the alignment film are qualified.

Alternatively, in the above method, the step S2 may further include:

step S23: converting the grey scale values of the first grey scale image regions indicated by the sign "a" into depth values of the alignment grooves based on a second predetermined correspondence; and step S24: comparing the obtained depth values of the alignment grooves with a predetermined reference depth threshold value, so as to determine whether the depths of the alignment grooves on the alignment film are qualified.

Alternatively, in the above method, the step S1 of generating a grey scale stripe image specifically includes steps of:

transmitting the rays onto a front side of the substrate 10 to generate a front side grey scale strep image, transmitting the rays onto a back side of the substrate 10 to generate a back side grey scale strep image; and combining the front side grey scale stripe image and the back side grey scale stripe image on the same region to obtain the grey scale stripe image for measuring the alignment grooves on the alignment film.

Alternatively, in the above method, the step S2 may further include:

step S25: changing an angle of the rays emitted by the ray source and detecting a corresponding region of the substrate again when the grey scale value of the region in the grey scale stripe image is greater than a predetermined grey scale threshold value.

The optional embodiments of the present disclosure have been discussed. It is appreciated that many modifications and polishes may be made to the present disclosure without departing from the principle of the present disclosure for those skilled in the art. These modifications and polishes should also be deemed to be fallen within the scope of the present disclosure.

What is claimed is:

1. An alignment film detecting device realized by a computer for detecting alignment grooves formed on an alignment film of a substrate, the alignment film detecting device comprising:
    an imaging circuit configured to obtain a grey scale stripe image of the alignment grooves on the alignment film of the substrate; and
    an image processing circuit configured to determine whether there is a defect in the alignment grooves on the alignment film through measuring depth values or width values of respective alignment grooves on the alignment film of the substrate by conducting an identification process on the grey scale stripe image based on the grey scale stripe image, and connected to the imaging circuit,
    wherein the imaging circuit comprises:
    a ray source configured to generate rays that are to be transmitted through the substrate comprising the alignment film; and
    a receiving circuit arranged to be opposite to a position of the ray source relative to the substrate, and configured to receive the rays having been transmitted through the substrate and generate a grey scale stripe image, wherein the grey scale stripe image comprises first grey scale image regions corresponding to the alignment grooves on the alignment film and second grey scale image regions corresponding to portions between every two neighboring ones of the alignment grooves, and the first grey scale image regions and the second grey scale image regions are arranged alternately.

2. The alignment film detecting device according to claim 1, wherein the image processing circuit comprises:
    a first measuring circuit configured to convert interface positions of the grey scale values representing gradient variation between the first grey scale image regions and the second grey scale image regions into width values of the alignment grooves on the alignment film based on a first predetermined correspondence; and
    a first determining circuit configured to compare the width values of the alignment grooves obtained by the first measuring circuit with a predetermined reference width threshold value, so as to determine whether the widths of the alignment grooves on the alignment film are qualified.

3. The alignment film detecting device according to claim 2, wherein
    the width values of the alignment grooves are each within a range of 0.05 µm-0.2 µm; and
    the alignment grooves are each of a straight stripe shape.

4. The alignment film detecting device according to claim 2, wherein the image processing circuit further comprises:
    a second measuring circuit configured to convert the grey scale values of the first grey scale image regions into depth values of the alignment grooves on the alignment films based on a second predetermined correspondence; and
    a second determining circuit configured to compare the depth values of the alignment grooves obtained by the second measuring circuit with a predetermined reference depth threshold value, so as to determine whether the depths of the alignment grooves on the alignment film are qualified.

5. The alignment film detecting device according to claim 1, wherein
    the ray source comprises an X-ray source configured to emit X rays; and
    the receiving circuit comprises an X-ray sensitive lens configured to receive the X rays and generate the grey scale stripe image based on the received X rays.

6. The alignment film detecting device according to claim 5, wherein a light diaphragm is arranged between the X-ray sensitive lens and the substrate and configured to adjust an intensity of the X-rays transmitted through the substrate, so as to stabilize a radiation amount of the X-rays received by the X-ray sensitive lens.

7. The alignment film detecting device according to claim 6, wherein the X-ray source consists of an X-ray array source; and
    the X-ray sensitive lens consists of an X-ray sensitive charge-coupled-device (CCD) flat panel detector (FPD).

8. The alignment film detecting device according to claim 2, wherein the image processing circuit further comprises:
    a third determining circuit configured to determine that there is a foreign substance in a detecting region when the grey scale values of the detecting region are greater than a predetermined grey scale threshold value.

9. The alignment film detecting device according to claim 1, wherein
    there are at least two imaging circuits, wherein the receiving circuit of any one of the imaging circuits receives the rays transmitted through the substrate and emitted by the ray source of another one of the imaging circuits, and generates the grey scale stripe image.

10. The alignment film detecting device according to claim 9, further comprising:
    a moving mechanism configured to move the imaging circuits to change an angle of the rays emitted by the ray source.

11. The alignment film detecting device according to claim 10, wherein
    the moving mechanism comprises an arc rail circularly extending from a side of the substrate to the other side of the substrate,
    wherein the imaging circuit is movable on the arc rail to change an angle of the rays that are incident on the substrate, and a position of the source ray relative to the substrate and a position of the receiving circuit relative to the substrate on the arc rail in the imaging circuit are exchangeable with each other, so as to combine a front-side grey scale stripe image generated by the rays being incident on a region of a front side of the substrate and a back-side grey scale stripe image generated by the rays being incident on the same region of a back side of the substrate.

12. The alignment film detecting device according to claim 7, wherein
    the X-ray sensitive CCD flat panel detector comprises: a lens driving device, an X-ray conversion screen and a CCD image rectangular plane sensor array;
    wherein after the X rays emitted by the X-ray source have been transmitted through the substrate, an intensity distribution of the X-rays carries information of the alignment film on the substrate, and the X-rays are incident on the X-ray conversion screen arranged opposite to the substrate, so as to be converted into a visible light image by the X-ray conversion screen;

wherein an intensity of visible light rays emitted from each point is proportional to radiation amount of the X-rays that are incident on the X-ray conversion screen, the X-ray conversion screen is in direct contact with a photosensitive surface of the CCD image rectangular plane sensor array, and the visible light rays emitted from the X-ray conversion screen is directly received by the photosensitive surface of the CCD image rectangular plane sensor array, so as to generate the grey scale stripe image; and wherein the grey scale stripe image is processed by an analog to digital (A/D) converter, and transmitted to the image processing circuit to gather, store and process image information, and then it is determined whether there is a defect in the alignment grooves based on the image information or other analyses are carried out.

13. The alignment film detecting device according to claim 12, wherein the imaging circuit further comprises: a high transparent prism and a cylindrical lens, wherein the X rays are emitted by the X-ray source under a control of an X-ray controller, adjusted by the cylindrical lens to be in a horizontal direction, reflected by the high transparent prism and incident on the substrate, transmitted through the substrate, and then incident on the X-ray conversion screen.

14. The alignment film detecting device according to claim 12, further comprising:

an image management circuit configured to manage the generated grey scale stripe image in classification, and establish an image database for the alignment grooves on the alignment film.

15. A method realized by a computer for detecting alignment grooves formed on an alignment film of a substrate, the method comprising steps of:

obtaining a grey scale stripe image of the alignment grooves on the alignment film of the substrate; and determining whether there is a defect in the alignment grooves on the alignment film through measuring depth values or width values of respective alignment grooves on the alignment film of the substrate by conducting an identification process on the grey scale stripe image based on the grey scale stripe image, wherein the step of obtaining the grey scale stripe image of the alignment grooves on the alignment film of the substrate comprises steps of:

generating rays that are to be transmitted through the substrate comprising the alignment film, receiving the rays having been transmitted through the substrate, and generating the grey scale stripe image, wherein the grey scale stripe image comprises first grey scale image regions corresponding to the alignment grooves and second grey scale image regions corresponding to portions between every two neighboring ones of the alignment grooves, and the first grey scale image regions and the second grey scale image regions are arranged alternately.

16. The method according to claim 15, wherein the step of determining whether there is a defect in the alignment grooves on the alignment film through measuring depth values or width values of respective alignment grooves on the alignment film of the substrate by conducting an identification process on the grey scale stripe image based on the grey scale stripe comprises steps of:

converting interface positions of the grey scale values representing gradient variation between the first grey scale image regions and the second grey scale image regions into width values of the alignment grooves on the alignment film based on a first predetermined correspondence; and comparing the width values of the alignment grooves with a predetermined reference width threshold value, so as to determine whether the widths of the alignment grooves on the alignment film are qualified.

17. The method according to claim 16, wherein the step of determining whether there is a defect in the alignment grooves on the alignment film through measuring depth values of width values of respective alignment grooves on the alignment film of the substrate by conducting an identification process on the grey scale stripe image based on the grey scale stripe image comprises steps of:

converting the grey scale values of the first grey scale image regions into depth values of the alignment grooves based on a second predetermined correspondence; and comparing the depth values of the alignment grooves with a predetermined reference depth threshold value, so as to determine whether the depths of the alignment grooves on the alignment film are qualified.

18. The method according to claim 15, wherein the step of generating the grey scale stripe image comprises steps of:

transmitting the rays onto a front side of the substrate to generate a front side grey scale stripe image, transmitting the rays onto a back side of the substrate to generate a back side grey scale stripe image; and combining the front side grey scale stripe image and the back side grey scale stripe image on the same region to obtain the grey scale stripe image for measuring the alignment grooves on the alignment film.

19. The method according to claim 16, further comprising:

changing an angle of the rays emitted by a ray source and detecting a corresponding region of the substrate when a grey scale value of the corresponding region in the grey scale stripe image is greater than a predetermined grey scale threshold value.

* * * * *